(12) United States Patent
Alsters

(10) Patent No.: US 10,040,732 B2
(45) Date of Patent: Aug. 7, 2018

(54) PROCESS FOR THE PRODUCTION OF BIARYL COMPOUNDS

(71) Applicant: DSM IP Assets B.V., Heerlen (NL)

(72) Inventor: Paulus Lambertus Alsters, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 23 days.

(21) Appl. No.: 15/326,860

(22) PCT Filed: Jul. 15, 2015

(86) PCT No.: PCT/EP2015/066183
§ 371 (c)(1),
(2) Date: Jan. 17, 2017

(87) PCT Pub. No.: WO2016/008931
PCT Pub. Date: Jan. 21, 2016

(65) Prior Publication Data
US 2017/0210681 A1 Jul. 27, 2017

(30) Foreign Application Priority Data

Jul. 17, 2014 (EP) .................................. 14177429
Feb. 11, 2015 (EP) .................................. 15154650

(51) Int. Cl.
C07C 2/84 (2006.01)
(52) U.S. Cl.
CPC ............ *C07C 2/84* (2013.01); *C07C 2531/22* (2013.01)

(58) Field of Classification Search
CPC .............................. C07C 2/84; C07C 2531/22
See application file for complete search history.

(56) References Cited

PUBLICATIONS

International Search Report for PCT/EP2015/066183 dated Oct. 6, 2015, 3 pages.
Yusuke Izawa and Shannon S. Stahl in "*Aerobic Oxidative Coupling of o-Xylene: Discovery of 2-Fluoropyridine as a Ligand to Support Selective Pd-Catalyzed C-H Functionalization,*" Published in Wiley-VCH Verlas GmbH & Co. KGaA, Weinheim, Madison, WI., vol. 352, No. 8, Published: Dec. 1, 2010, pp. 3223-3229.
Advanced Synthesis & Catalysis, "*Supporting Information for Aerobic Oxidative Coupling of o-Xylene: Discovery of 2-Fluoropyridine as a Ligand to Support Selective Pd-Catalyzed C-H Functionalization*", Published in Wiley-VCH Verlas GmbH & Co. KGaA, Weinheim, Madison, WI., Published: Dec. 1, 2010, pp. S1-S30.

*Primary Examiner* — Brian A McCaig
*Assistant Examiner* — Jason Y Chong
(74) *Attorney, Agent, or Firm* — Nixon & Vanderhye P.C.

(57) ABSTRACT

Process for producing biaryl compounds by aerobic cross dehydrogenative coupling (CDC) of two arene groups comprising at least one aryl carbon-hydrogen bond, in the presence of a catalyst system comprising a palladium salt comprising at least one non-cyclopalladatable carboxylate anion and one or more non-beta-eliminatable, non-cyclopalladatable ligands comprising at least one N-donor atom, the one or more ligands having a 0.5/1-1.5/1 molar ratio of N-donor atoms relative to the Pd atoms.

15 Claims, No Drawings

PROCESS FOR THE PRODUCTION OF BIARYL COMPOUNDS

This application is the U.S. national phase of International Application No. PCT/EP2015/066183 filed Jul. 15, 2015 which designated the U.S. and claims priority to EP Patent Application No. 14177429.9 filed Jul. 17, 2014 and claims priority to EP Patent Application No. 15154650.4 filed Feb. 11, 2015 the entire contents of each of which are hereby incorporated by reference.

The invention relates to a process for the production of biaryl compounds.

Biaryl compounds constitute an important class of compounds with a variety of applications, e.g. in market segments related to pharmaceuticals, agrochemicals, electronic chemicals and polymers.

Especially for bulk applications, for example as monomer units in polymers, it is important to produce the biaryl compounds at low costs.

Known processes for the production of biaryl compounds based on the coupling of two substituted arene units with prior activation of the arene units are in general not commercially viable. This is because the process requires many steps and expensive reagents, and it also generates large amounts of salt water.

An improvement was provided by a process for the production of biaryl compounds by cross dehydrogenative coupling (CDC) of two arene units, as recently reviewed in *Chem. Asian J.* 2014, 9, 26. As is illustrated in this paper, such a process does not require prior activation of the arene units and it is economic, especially if oxygen is used as oxidant. Such a process is called aerobic CDC. Palladium (Pd) catalyzed aerobic CDC is already used commercially for coupling of dimethyl phthalate to produce tetramethyl [1,1'-biphenyl]-3,3',4,4'-tetracarboxylate, an intermediate for polyimide resins.

As explained in *Adv. Synth. Catal.* 2010, 352, 3223, this process could be significantly streamlined by carrying out the CDC of ortho-xylene, followed by aerobic oxidation of the benzylic methyl groups of the coupling product 3,3',4,4'-tetramethyl-1,1'-biphenyl (3344). This paper discloses an aerobic CDC catalyst system comprising a palladium dicarboxylate salt and a pyridine ligand used in a 2/1 molar ratio relative to Pd. In particular 2-fluoropyridine is used as ligand, being an efficient, though expensive pyridine. In high volume, low cost applications such as those for the manufacture of bulk monomers, minimizing catalyst costs is essential to meet the strict cost price requirements. It is therefore desirable to have efficient palladium arene CDC catalysts that operate efficiently with significantly less, preferable also simpler nitrogen donor ligands. It is also desirable to obtain a CDC process with improved activity and selectivity.

Surprisingly this aim is achieved by a process for producing biaryl compounds by aerobic CDC of two arene groups comprising at least one aryl carbon-hydrogen bond, in the presence of a catalyst system comprising a palladium salt comprising at least one non-cyclopalladatable carboxylate anion and one or more non-beta-eliminatable, non-cyclopalladatable ligands comprising at least one N-donor atom, the one or more ligands having a 0.5/1-1.5/1 molar ratio of N-donor atoms relative to the Pd atoms (also indicated by the abbreviation N/Pd ratio from here on).

With a non-cyclopalladatable carboxylate anion is meant a carboxylate anion devoid of C—H bonds prone to cleavage by palladium, typically leading to 5 or 6 membered rings with a C,O-donor set linked to the Pd center, with the C-atom originating from the C—H bond that is cleaved. Examples of benzoate- or phenylacetate-type carboxylate anions prone to cyclopalladation have been described in *J. Am. Chem. Soc.* 2008, 130, 14082.

With a non-beta-eliminatable nitrogen donor ligand is meant a nitrogen donor ligand that does not induce reduction of palladium(II) to palladium(0) via beta-hydride elimination from a Pd—N—C—H fragment, with the N—C—H fragment being part of the nitrogen donor ligand that is bound to palladium. Nitrogen donor ligands prone to beta-hydride elimination include trialkylamines containing a N—C—H fragment, such as found in for example tributylamine as described in *Chemistry* 2011, 17, 3091.

With a non-cyclopalladatable nitrogen donor ligand is meant a nitrogen donor ligand devoid of C—H bonds prone to cleavage by palladium, typically leading to 5 or 6 membered rings with a C,N-donor set linked to the Pd center, with the C-atom originating from the C—H bond that is cleaved. Nitrogen donor ligands prone to cyclopalladation via C—H cleavage are well known, and examples can, among others, be found in *Chem. Rev.* 2005, 105, 2527 and in *Palladacycles* 2008, 13, which also clarify rules for their formation.

With the process of the invention improved results in terms of catalyst activity and/or selectivity are obtained even with simple ligands, resulting in lower costs.

Preferably the ratio of N-donor atoms relative to the Pd atoms is between 0.7/1 and 1.3/1, more preferably between 0.8/1 and 1.2/1.

Good results are obtained when aliphatic cyclic or non-cyclic primary, secondary or tertiary amines, aromatic N-heterocycles and/or benzofused derivatives thereof are used as the one or more ligands. Preferably N-heterocycles and benzofused derivatives thereof are used that contain a $sp^2$ hybridized nitrogen atom with the lone electron pair on the nitrogen atom positioned in-plane with respect to the plane formed by the X—N—Y group, where X and Y denote the atoms directly bound to the $sp^2$ nitrogen atom. Even more preferably N-heterocyclic compounds are used that contain a $sp^2$ hybridized nitrogen atom with the lone electron pair on the nitrogen atom positioned in-plane with respect to the plane formed by the X—N—Y group, where X and Y denote the atoms directly bound to the $sp^2$ nitrogen atom and either X or Y being a carbon atom. From above defined preferred group even more preferably pyridines, pyridazines, pyrimidines, pyrazines, triazines, imidazoles, triazoles, oxazoles, 4,5-dihydrooxazoles, isoxazoles, 4,5-dihydroisoxazoles, and 5,6-dihydro-4H-1,3-oxazines or quinolines, isoquinolines, cinnolines, phthalazines, quinazoline, quinoxalines, 1H-benzo[d]imidazoles, 1H-benzo[d][1,2,3]triazoles, benzo[d]oxazoles, benzo[d]isoxazoles and 4H-benzo[e][1,3]oxazines and/or benzofused derivatives thereof are used as ligand.

Even more preferably aromatic 6 membered ring N-heterocycles or benzofused derivatives thereof are used as the one or more ligands. Preferably in this group pyridines, pyridazines, pyrimidines, pyrazines, triazines, quinolines, isoquinolines, cinnolines, phthalazine, quinazoline and quinoxalines and/or benzofused derivatives thereof are used as the one or more ligands.

The nitrogen donor ligand may be further substituted to control the activity and/or the selectivity of the palladium catalyst. The optimum choice of the substituent depends among others on the nature of the palladium salt and on the required regioselectivity of the arene CDC process, which is determined by the final application. When the final application requires the CDC of ortho-xylene to be directed towards the asymmetrical 2,3,3',4'-tetramethyl-1,1'-biphenyl (2334) regioisomer instead of symmetrical 3344 that is for example required as monomer intermediate, it is advantageous to use a non-cyclopalladatable pyridine with at least one electron-withdrawing, non-coordinating, preferably bulky ortho-substituent as the one or more ligands.

Surprisingly it was found that if the process is carried out under relatively low (partial) pressures of oxygen of 0.2-2 bar, even further increased activity and selectivity is obtained if a palladium carboxylate catalyst is used containing at least one non-cyclopalladatable carboxylate anion derived from a carboxylic acid that is triply substituted at the alpha-carbon atom relative to the carboxylate group, with the carboxylic acid also containing at least one beta-carbon atom.

It was also surprisingly found that if the process is carried out under relatively low (partial) pressures of oxygen of 0.2-2 bar, even further increased activity and selectivity is obtained if a palladium carboxylate catalyst is used containing at least one non-cyclopalladatable carboxylate anion derived from a carboxylic acid with an acidity constant ($pK_a$) in between that of acetic acid and 2,2,2-trifluoroacetic acid, with aforementioned acidity constant meaning the acidity constant average ($pK_a^{acid\ 1}+pK_a^{acid\ 2}$)/2 in case of two different carboxylate anions.

It is also possible to use carboxylate anions derived from triply substituted carboxylic acids as defined above that also have an acidity constant ($pK_a$) in between that of acetic acid and 2,2,2-trifluoroacetic acid, with aforementioned acidity constant meaning the acidity constant average ($pK_a^{acid\ 1}+pK_a^{acid\ 2}$)/2 in case of two different carboxylate anions.

Preferably as the carboxylic acids that are triply substituted at the alpha-carbon atom relative to the carboxylate group, with such carboxylic acids also containing at least one beta-carbon atom, are used: 2,2-dialkylalkanoic acids, 2-fluoro-2-alkylalkanoic acids, 2,2-difluoroalkanoic acids, 2,2-difluoro-2-arylacetic acids, with the aforementioned alkanoic acids containing at least one beta-carbon atom. The alkyl is preferably a methyl or perfluoroalkyl group, most preferably a trifluoromethyl group. The aryl group is preferably a phenyl group.

Even more preferably as the carboxylic acids that are triply substituted at the alpha-carbon atom relative to the carboxylate group, with such carboxylic acids also containing at least one beta-carbon atom, are used: pivalic acid, 3,3,3-trifluoro-2-methyl-2-(trifluoromethyl)propanoic acid, 3,3,3-trifluoro-2,2-bis(trifluoromethyl)propanoic acid, and 2,2-difluoro-2-phenylacetic acid.

Preferably as the carboxylic acids with an acidity constant in between that of acetic acid and 2,2,2-trifluoroacetic acid are used: 2,2-difluoroacetic acid, 2-fluoroacetic acid, 2,2,3,3-pentafluoropropanoic acid, 2,2,3,3-tetrafluoropropanoic acid, 2,3,3,3-tetrafluoropropanoic acid, 2,2,3-trifluoropropanoic acid, 2,3,3-trifluoropropanoic acid, 3,3,3-trifluoropropanoic acid, 2,2-difluoropropanoic acid, 2,3-difluoropropanoic acid, 3,3-difluoropropanoic acid, 2-fluoropropanoic acid, 3-fluoropropanoic acid, 3,3,3-trifluoro-2-methyl-2-(trifluoromethyl)propanoic acid, 3,3,3-trifluoro-2,2-bis(trifluoromethyl)propanoic acid, 3,3,3-trifluoro-2-(trifluoromethyl) propanoic acid, 2,3,4,5,6-pentafluorobenzoic acid, 2,3,4,5-tetrafluorobenzoic acid, 2,3,4,6-tetrafluorobenzoic acid, 2,3,5,6-tetrafluorobenzoic acid, 2,3,4-trifluorobenzoic acid, 2,3,5-trifluorobenzoic acid, 2,3,6-trifluorobenzoic acid, 2,4,5-trifluorobenzoic acid, 2,4,6-trifluorobenzoic acid, 3,4,5-trifluorobenzoic acid, 2,3-difluorobenzoic acid, 2,4-difluorobenzoic acid, 2,5-difluorobenzoic acid, 2,6-difluorobenzoic acid, 3,4-difluorobenzoic acid, 3,5-difluorobenzoic acid, 3,4,5-tris(trifluoromethyl)benzoic acid, 3,4-bis(trifluoromethyl)benzoic acid, 3,5-bis(trifluoromethyl) benzoic acid, 2,2-difluoro-2-phenylacetic acid, 2-(2,3,4,5,6-pentafluorophenyl)acetic acid, 2-nitroacetic acid, 2,3-dinitrobenzoic acid, 2,4-dinitrobenzoic acid, 2,5-dinitrobenzoic acid, 3,4-dinitrobenzoic acid, 3,5-dinitrobenzoic acid, 2-nitro-benzoic acid, 3-nitrobenzoic acid, and 4-nitrobenzoic acid.

Even more preferably as the carboxylic acids with an acidity constant in between that of acetic acid and 2,2,2-trifluoroacetic acid are used: 2,2-difluoroacetic acid, 2,2-difluoropropionic acid, 3,3,3-trifluoro-2-methyl-2-(trifluoromethyl)propanoic acid, 3,3,3-trifluoro-2,2-bis (trifluoromethyl)propanoic acid, 2,3,4,5,6-pentafluorobenzoic acid, 2,2-difluoro-2-phenylacetic acid, 2-(2,3,4,5,6-pentafluorophenyl)acetic acid 2,4-dinitrobenzoic acid, 2,5-dinitrobenzoic acid, and 3,4-dinitrobenzoic acid.

Surprisingly it was also found that if the process is carried out under relatively high (partial) pressures of oxygen of 2-20 bar, even further increased activity and selectivity is obtained if a palladium catalyst is used containing at least one non-cyclopalladatable carboxylate anion derived from a strongly acidic carboxylic acid, i.e. with an acidity constant that is equal or less than the acidity constant average of acetic acid and 2,2,2-trifluoroacetic acid, with aforementioned acidity constant average being quantified as ($pK_a^{acetic\ acid}+pK_a^{trifluoroacetic\ acid}$)/2.

Preferably as the strongly acidic carboxylic acids with an acidity constant that is equal or less than the acidity constant average of acetic acid and 2,2,2-trifluoroacetic acid are used: 2,2,2-trifluoroacetic acid, 2,2-difluoroacetic acid, 2,2,3,3,3-pentafluoropropanoic acid, 2,2,3,3-tetrafluoropropanoic acid, 2,3,3,3-tetrafluoropropanoic acid, 2,2,3-trifluoropropanoic acid, 2,2-difluoropropanoic acid, 3,3,3-trifluoro-2,2-bis(trifluoromethyl)propanoic acid, 3,3,3-trifluoro-2-(trifluoromethyl)propanoic acid, 2,3,4,5,6-pentafluorobenzoic acid, 2,3,4,6-tetrafluorobenzoic acid, 2,3,5,6-tetrafluorobenzoic acid, 2,3,6-trifluorobenzoic acid, 2,4,6-trifluorobenzoic acid, 2,2-difluoro-2-phenylacetic acid, 2,4-dinitrobenzoic acid, and 2,6-dinitrobenzoic acid.

More preferably as the strongly acidic carboxylic acids with an acidity constant that is equal or less than the acidity constant average of acetic acid and 2,2,2-trifluoroacetic acid are used: trifluoroacetic acid, 3,3,3-trifluoro-2,2-bis(trifluoromethyl)propanoic acid, 3,3,3-trifluoro-2-(trifluoromethyl) propanoic acid, and 2,2-difluoro-2-phenylacetic acid.

An even further improved process with respect to activity and selectivity under relatively high (partial) pressures of oxygen of 2-20 bar is obtained, if the carboxylate anion is derived from a carboxylic acid that is both strongly acidic as defined above and that is triply substituted at the alpha-carbon atom relative to the carboxylate group, with the carboxylic acid also containing at least one beta-carbon atom.

Preferably as the carboxylic acids that are both strongly acidic as defined above and that are triply substituted at the alpha-carbon atom relative to the carboxylate group, with the carboxylic acids also containing at least one beta-carbon atom are used: 3,3,3-trifluoro-2,2-bis(trifluoromethyl)propanoic acid, 3,3,3-trifluoro-2-(trifluoromethyl)propanoic acid, and 2,2-difluoro-2-phenylacetic acid.

Efficient palladium carboxylate catalysts may also be generated in situ, for example by anion exchange between a palladium salt and a carboxylate salt derived from such a triply substituted carboxylic acid as defined above, or derived from a carboxylic acid with an acidity constant in between that of acetic acid and 2,2,2-trifluoroacetic acid, or derived from a strongly acidic carboxylic acid with an acidity constant that is equal or less than the acidity constant average of acetic acid and 2,2,2-trifluoroacetic acid as defined above. In situ catalyst generation by anion exchange may also proceed between a palladium salt and such a triply substituted carboxylic acid as defined above, or a carboxylic acid with an acidity constant in between that of acetic acid and 2,2,2-trifluoroacetic acid, or a strongly acidic carboxylic acid with an acidity constant that is equal or less than the acidity constant average of acetic acid and 2,2,2-trifluoroacetic acid as defined above. Anion exchange between a palladium salt and a carboxylic acid proceeds most efficiently by using an excess of the carboxylic acid relative to the palladium salt when the latter is derived from an acid with a strength that is comparable to that of the carboxylic acid, or when the palladium salt (e.g. $Pd[MeCO_2]_2$) is derived from an acid that is weaker than the carboxylic acid.

Palladium dicarboxylate catalysts may also contain two different carboxylate anions, for example one carboxylate anion derived from a triply substituted carboxylic acid as defined above, and a carboxylate anion derived from a carboxylic acid with an acidity constant in between that of acetic acid and 2,2,2-trifluoroacetic acid, or derived from a strongly acidic carboxylic acid with an acidity constant that is equal or less than the acidity constant average of acetic acid and 2,2,2-trifluoroacetic acid as defined above. Such palladium dicarboxylate catalysts with different carboxylate anions may also be generated in situ by anion exchange between for example two different palladium dicarboxylates, or by anion exchange between for example a palladium salt and a carboxylic acid.

As solvents acetic acid, propionic acid or propylene carbonate may be used. Preferably acetic acid or propylene carbonate is used. If acetic acid or propionic acid is used while the process is carried out under relatively low (partial) pressures of oxygen of 0.2-2 bar, preferably a carboxylate anion is used derived from a carboxylic acid having an acidity constant that is equal or less than $(pK_a^{acetic\ acid} + pK_a^{trifluoroacetic\ acid})/2$, but greater than $pK_a^{trifluoroacetic\ acid}$, or two different carboxylate anions are used derived from two different carboxylic acids whose acidity constant average $(pK_a^{acid\ 1} + pK_a^{acid\ 2})/2$ is equal or less than $(pK_a^{acetic\ acid} + pK_a^{trifluoroacetic\ acid})/2$, but greater than $pK_a^{trifluoroacetic\ acid}$.

A further advantage of the process according to the invention is that good results in terms of activity and selectivity are obtained if the process is carried out with a low amount of solvent or even without a solvent. Preferably at most 50 wt % of solvent is used, based on the total reaction mass, more preferably at most 25 wt %, even more preferably at most 10 wt %, even more preferably at most 5 wt %, even more preferably at most 2 wt %. Most preferably no solvent at all is used. In this way only a small amount of solvent or no solvent at all needs to be separated from the reaction mixture after completion of the reaction. It also means that the productivity per unit of reactor volume is higher (higher space time yield).

Optionally additives may be added. These additives may improve the activity, stability, or selectivity of the catalyst. Examples of such additives are Lewis acids, such as metal triflates, or strong Brønsted acids. Other examples of potentially beneficial additives are redox active compounds that inhibit catalyst deactivation by formation of metallic palladium. Such redox active compounds include copper(II) salts, vanadium-containing polyoxometalates, or organic electron acceptors such as benzoquinones.

The CDC process according to this invention is preferably carried out at temperatures above room temperature. The optimum temperature depends on the nature of the arene coupling partner(s) and the required selectivity, in particular the required regioselectivity. Preferably, the reaction temperature is between 70 and 200° C., most preferably between 90 and 180° C. The preferred oxygen pressure depends on the available infrastructure and the nature of the CDC reaction. Preferably, the CDC process according to the invention is carried out in such a way that either the explosion risk is eliminated (e.g. by operating a semi-batch reactor via continuous supply of an oxygen/nitrogen mixture with a composition below the oxygen limit concentration), or the impact of an unintended explosion is minimized to an acceptable level (e.g. by operating a continuous flow tube reactor with oxygen or a minimum-headspace semi-batch reactor via continuous supply of oxygen).

The CDC process according to this invention may involve a homocoupling (i.e. with a single arene that is coupled to form a biaryl product) or a heterocoupling (i.e. with two different arene coupling partners). CDC processes of these types according to this invention may be either intermolecular or intramolecular.

Examples of suitable arenes in homo- or heterocoupling processes according to this invention are arenes (such as benzene, naphthalene, anthracene, phenanthrene), alkylarenes (such as toluene, 1-methylnaphthalene, 2-methylnapthalene, ortho-xylene, meta-xylene, para-xylene, ethylbenzene, cumene, tert.-butylbenzene, diphenylmethane, propane-2,2-diyldibenzene), aryl carboxylic acid esters (such as methyl benzoate, methyl 1-naphthoate, methyl 2-naphthoate, dimethyl phthalate, methyl ortho-toluate, methyl meta-toluate, methyl para-toluate, dimethyl isophthalate, dimethyl terephthalate), haloarenes (such as fluorobenzene, 1-fluoronaphthalene, 2-fluoronaphthalene, chlorobenzene, 1-chloronaphthalene, 2-chloronaphthalene), aryl ethers (such as anisole, 1-methoxynaphthalene, 2-methoxynaphthalene, diphenylether), and diaryl amines (such as N,N-diphenylacetamide). The arene in a homocoupling process according to this invention may also be a heteroarene, as long as the heteroarene does not have a heteroatom that interferes negatively in the CDC process, e.g. by competing with the nitrogen donor ligand in its coordination to the palladium salt. Examples of suitable heteroarenes can be found in *Chem. Asian J.* 2014, 9, 26 (such as furans, thiophenes, pyrroles, pyridine-N-oxides, and benzofused derivatives thereof).

EXAMPLES

In the following examples dealing with CDC of ortho-xylene, regioselectivity is defined as 100%*yield(3344)/[yield(2334)+yield(3344)], whereas chemoselectivity is defined as 100%*[yield(2334)+yield(3344)]/[yield(2334)+yield(3344)+yield(Bald)], with 3344 meaning 3,3',4,4'-tetramethyl-1,1'-biphenyl, 2334 meaning 2,3,3',4'-tetramethyl-1,1-biphenyl, and Bald meaning 2-methylbenzaldehyde. Activity is defined as the combined 2334+3344 yield obtained in a given amount of reaction time.

Gas Chromatography (GC) measurements were carried out on an Agilent 6890 instrument equipped with an Agilent HP-5 column (length, 30 m; diameter, 0.32 mm; film, 0.25 μm). Settings: initial temperature, 80° C. (1 min); ramp rate, 20° C./min; final temperature, 300° C. (3 min). Retention times (min): Bald, 4.04; hexadecane internal standard, 7.45; 2334, 8.45; 3344, 9.04.

Example 1.1-1.12

CDC in a solvent using various ligands, N/Pd molar ratio is 1/1.

Examples 1.1-1.12 relate to the CDC of ortho-xylene in propylene carbonate as solvent under 1 bar $O_2$ catalyzed by in situ generated $Pd[MeCO_2][CF_3CO_2]$ in the presence of a ligand added in an amount that corresponds to 1 equivalent of N-donor atoms relative to Pd.

For each example a mixture of ortho-xylene (1.0 mL), dry propylene carbonate (1.0 mL), $Pd[MeCO_2]_2$ (1.0 mol %), $CF_3CO_2H$ (0.8 mol %), and a ligand as indicated in table 1 (1.0 mol % of N-donor atoms) was stirred for 16 hrs at 85° C. (external temperature) in a reaction tube under 1 bar $O_2$. The reaction mixture was diluted and a sample was subsequently analyzed by GC, using hexadecane as internal standard. A slight deficiency of $CF_3CO_2H$ relative to the amount required to fully convert $Pd[MeCO_2]_2$ into $Pd[MeCO_2][CF_3CO_2]$ was used in order to suppress unintended acid-catalyzed hydrolysis of pyridine ligand 9 with an ester group. The results are shown in Table 1.

Comparative Experiments A.1-A.12

CDC in a solvent using various ligands, N/Pd molar ratio is 2/1.

As examples 1.1-1.12, however the N/Pd molar ration is 2/1. The ligands and the results are shown in Table 1.

Comparison of examples 1.1-1.12 with comparative experiments A.1-A.12 shows that activities increase significantly on reducing the N/Pd ratio from 2/1 to 1/1. The data in Table 1 also illustrate the control of activity and selectivity by the substituent pattern of a ligand (cf. example 1.1 with examples 1.2-1.9).

TABLE 1

| Example/Comp. Exp.: | 1.1 | A.1 | 1.2 | A.2 | 1.3 | A.3 | 1.4 | A.4 |
|---|---|---|---|---|---|---|---|---|
| Ligand: | pyridine | pyridine | 2-Me-pyridine | 2-Me-pyridine | 5-CF₃-2-Me-pyridine | 5-CF₃-2-Me-pyridine | 2-Me-6-F-pyridine | 2-Me-6-F-pyridine |
| Yield (%) 2334 + 3344: | 4.88 | 0.06 | 3.89 | 0.09 | 6.06 | 1.96 | 5.80 | 5.05 |
| Yield (%) Bald: | 0.37 | 0.03 | 0.10 | 0.02 | 0.11 | 0.16 | 0.10 | 0.10 |
| Regioselectivity (%): | 85 | 83 | 86 | 89 | 86 | 83 | 81 | 81 |
| Chemoselectivity (%): | 93 | 67 | 97 | 82 | 98 | 92 | 98 | 98 |

| Example/Comp. Exp.: | 1.5 | A.5 | 1.6 | A.6 | 1.7 | A.7 | 1.8 | A.8 |
|---|---|---|---|---|---|---|---|---|
| Ligand: | 2-F-pyridine | 2-F-pyridine | 4-CF₃-pyridine | 4-CF₃-pyridine | 4-OMe-pyridine | 4-OMe-pyridine | 2-OMe-pyridine | 2-OMe-pyridine |
| Yield (%) 2334 + 3344: | 7.01 | 6.13 | 5.12 | 0.88 | 4.39 | 0.03 | 0.68 | 0.15 |
| Yield (%) Bald: | 0.05 | 0.07 | 0.26 | 0.16 | 0.33 | 0.03 | 0.03 | 0.02 |
| Regioselectivity (%): | 82 | 85 | 85 | 89 | 86 | 100 | 76 | 80 |
| Chemoselectivity (%): | 99 | 99 | 95 | 85 | 93 | 50 | 96 | 88 |

| Example/Comp. Exp.: | 1.9 | A.9 | 1.10 | A.10 | 1.11 | A.11 | 1.12 | A.12 |
|---|---|---|---|---|---|---|---|---|
| Ligand: | 2-CH₂CO₂Et-pyridine | 2-CH₂CO₂Et-pyridine | quinuclidine | quinuclidine | Pr-NH-Me | Pr-NH-Me | Bu-NH₂ | Bu-NH₂ |
| Yield (%) 2334 + 3344: | 0.81 | 0.00 | 1.18 | 0.05 | 0.76 | 0.01 | 1.93 | 0.61 |
| Yield (%) Bald: | 0.07 | 1.31 | 0.15 | 0.20 | 0.03 | 0.02 | 0.04 | 0.04 |
| Regioselectivity (%): | 83 | — | 76 | 80 | 80 | 100 | 84 | 87 |
| Chemoselectivity (%): | 92 | 0 | 89 | 20 | 96 | 33 | 98 | 94 |

Examples 2.1 and 2.2

As examples 1.1-1.2, but as ligands 2-(trifluoromethyl) pyridine or 2,6-difluoropyridine were used. The results are shown in Table 2.

TABLE 2

| Example: | 2.1 | 2.2 |
|---|---|---|
| Ligand: | 2-(trifluoromethyl)pyridine | 2,6-difluoropyridine |
| Yield (%) 2334 + 3344: | 1.94 | 2.18 |
| Yield (%) Bald: | 0.08 | 0.08 |
| 2334/3344: | 0.52 | 0.66 |

These experiments show that even better results are obtained if a non-cyclopalladatable pyridine is used with at least one electron-withdrawing, non-coordinating, preferably bulky ortho-substituent as nitrogen donor ligand when the final application requires the CDC of ortho-xylene to be directed towards the asymmetrical 2334 regioisomer instead of the symmetrical 3344 regioisomer. This conclusion can be drawn from a comparison with data shown in Table 1 with for example either 1 eq of pyridine or 4-(trifluoromethyl) pyridine as ligand (examples 1.1 and 1.6), both affording a 2334/3344 biaryl regioisomer ratio of only 0.17 instead of 0.52 obtained with 1 eq of 2-(trifluoromethyl)pyridine (example 2.1.) or 0.66 obtained with 1 eq of 2,6-difluoropyridine as nitrogen donor ligand (example 2.2), with 2334/3344=[100/Regioselectivity]−1.

Examples 3.1-3.15

CDC without solvent using various ligands and carboxylate anions at low pressure.

Example 3 relates to cross dehydrogenative coupling of ortho-xylene without solvent under 1 bar $O_2$ catalyzed by (in situ generated) palladium carboxylates in the presence of a ligand added in an amount that corresponds to 1 equivalent of N-donor atoms relative to Pd.

A mixture of ortho-xylene (2.0 mL), palladium carboxylate(s) (total 0.5 mol % of Pd), optionally a carboxylic acid additive (amount indicated in Table 3), and ligand (0.5 mol % of N-donor atoms) was stirred for 3 hrs at 85° C. (external temperature; 2 hrs for example 3.12) in a reaction tube under 1 bar $O_2$. The reaction mixture was diluted and a sample was subsequently analyzed by GC, using hexadecane as internal standard. The ligands, the carboxylates and the results are shown in Table 3.

Table 3 shows examples of in situ generated palladium carboxylate catalysts by anion exchange, either by anion exchange between two palladium dicarboxylate salts (example 3.5), or by anion exchange between a palladium dicarboxylate salt and a carboxylic acid (examples 3.7-3.9, 3.11, 3.12, 3.14, and 3.15).

Examples 3.1, 3.3, and 3.5 illustrate the increase in activity and regioselectivity when palladium carboxylate catalysts containing non-cyclopalladatable carboxylate anions derived from carboxylic acids that are triply substituted at the alpha-carbon atom relative to the carboxylate group, with the carboxylic acids also containing at least one beta-carbon atom, are used instead of palladium carboxylate catalysts containing non-cyclopalladatable carboxylate anions derived from carboxylic acids devoid of such triply substituted carboxylate groups, as in examples 3.13-3.15.

Examples 3.3, 3.5-3.11, and 3.14 illustrate the increase in activity and regio- or chemoselectivity when palladium carboxylate catalysts containing at least one non-cyclopalladatable carboxylate anion derived from a carboxylic acid with an acidity constant in between that of acetic acid and 2,2,2-trifluoroacetic acid, with aforementioned acidity constant meaning the acidity constant average ($pK_a^{acid\ 1}+pK_a^{acid\ 2}$)/2 in case of two different carboxylate anions, are used instead of palladium carboxylate catalysts containing non-cyclopalladatable carboxylate anions derived from carboxylic acids with an acidity outside this acidity range, as in examples 3.13 and 3.15).

The data in Table 3 also illustrate the control of activity and selectivity by the substituent pattern of a ligand (cf. example 3.1 with 3.2; example 3.3 with 3.4).

Furthermore, the data in Table 3 illustrate that chemoselectivity (cf. example 3.6 with 3.9; example 3.13 with 3.14; example 3.13 with 3.15) and/or activity (cf. example 3.13 with 3.14) may benefit from the addition of a strong acid to a palladium carboxylate catalyst.

TABLE 3

| Example: | 3.1 | 3.2 | 3.3 | 3.4 |
|---|---|---|---|---|
| Pd salt (mol %): | Pd[tBuCO$_2$]$_2$ (0.5) | Pd[tBuCO$_2$]$_2$ (0.5) | Pd[Me(CF$_3$)$_2$CCO$_2$]$_2$ (0.5) | Pd[Me(CF$_3$)$_2$CCO$_2$]$_2$ (0.5) |
| Ligand: | 4-(CF$_3$)pyridine | 3,5-bis(CF$_3$)pyridine | 4-(CF$_3$)pyridine | 3,5-bis(CF$_3$)pyridine |
| Yield (%) 2334 + 3344: | 0.91 | 1.81 | 3.07 | 2.13 |
| Yield (%) Bald: | 0.23 | 0.58 | 0.64 | 0.38 |
| Regioselectivity (%): | 97 | 95 | 93 | 92 |
| Chemoselectivity (%): | 80 | 76 | 83 | 85 |

TABLE 3-continued

| Example: | 3.5 | 3.6 | 3.7 | 3.8 |
|---|---|---|---|---|
| Pd salt 1 (mol %): | Pd[tBuCO$_2$]$_2$ (0.25) | Pd[3,5-(CF$_3$)$_2$C$_6$H$_3$CO$_2$]$_2$ (0.5) | Pd[MeCO$_2$]$_2$ (0.5) | Pd[MeCO$_2$]$_2$ (0.5) |
| Pd salt 2 (mol %): | Pd[Me(CF$_3$)$_2$CCO$_2$]$_2$ (0.25) | — | — | — |
| Additive (mol %): | — | — | 3,5-(CF$_3$)$_2$C$_6$H$_3$CO$_2$H (1.0) | 3,5-(CF$_3$)$_2$C$_6$H$_3$CO$_2$H (0.5) |
| Ligand: | 4-CF$_3$-pyridine | 4-CF$_3$-pyridine | 4-CF$_3$-pyridine | 4-CF$_3$-pyridine |
| Yield (%) 2334 + 3344: | 1.28 | 1.44 | 1.21 | 0.76 |
| Yield (%) Bald: | 0.43 | 0.42 | 0.43 | 0.28 |
| Regioselectivity (%): | 93 | 90 | 93 | 91 |
| Chemoselectivity (%): | 75 | 77 | 74 | 73 |

| Example: | 3.9 | 3.10 | 3.11 | 3.12 (Note) |
|---|---|---|---|---|
| Pd salt (mol %): | Pd[3,5-(CF$_3$)$_2$C$_6$H$_3$CO$_2$]$_2$ (0.5) | Pd[3,4-(CF$_3$)$_2$C$_6$H$_3$CO$_2$]$_2$ (0.5) | Pd[MeCO$_2$]$_2$ (0.5) | Pd[MeCO$_2$]$_2$ (0.5) |
| Additive (mol %): | CF$_3$CO$_2$H (0.5) | — | 3-CF$_3$C$_6$H$_4$CO$_2$H (1.0) | PhCF$_2$CO$_2$H (1.0) |
| Ligand: | 4-CF$_3$-pyridine | 4-CF$_3$-pyridine | 4-CF$_3$-pyridine | pyridine |
| Yield (%) 2334 + 3344: | 1.40 | 2.09 | 0.84 | 2.84 |
| Yield (%) Bald: | 0.10 | 0.55 | 0.30 | 0.60 |
| Regioselectivity (%): | 86 | 90 | 94 | 92 |
| Chemoselectivity (%): | 93 | 79 | 74 | 83 |

| Example | 3.13 | 3.14 | 3.15 |
|---|---|---|---|
| Pd salt (mol %): | Pd[MeCO$_2$]$_2$ | Pd[MeCO$_2$]$_2$ (0.5) | Pd[MeCO$_2$]$_2$ (0.5) |
| Additive (mol %): | — | CF$_3$CO$_2$H (0.5) | CF$_3$CO$_2$H (1.0) |
| Ligand: | 4-CF$_3$-pyridine | 4-CF$_3$-pyridine | 4-CF$_3$-pyridine |
| Yield (%) 2334 + 3344: | 0.07 | 0.50 | 0.07 |
| Yield (%) Bald: | 0.01 | 0.03 | <0.01 |
| Regioselectivity (%): | 88 | 85 | 79 |
| Chemoselectivity (%): | 88 | 95 | 96 |

Note
Example 12: Yields after 2 hrs as measured by GC.

Examples 4.1-4.9

CDC without solvent using various ligands and carboxylate anions at high pressure.

A mixture of ortho-xylene (1.0 mL), palladium carboxylate (0.5 mol % of Pd), optionally a carboxylic acid additive (amount indicated in Table 4), and ligand (0.5 mol % of N-donor atoms) was stirred for ~2.5 hrs at 85° C. (external temperature) in an autoclave under 11 bar O$_2$. The reaction mixture was diluted and a sample was subsequently analyzed by GC, using hexadecane as internal standard. The results are shown in Table 4.

Examples 4.2, 4.3, and 4.5-4.7 provide examples of in situ generated palladium carboxylate catalysts by anion exchange between a palladium dicarboxylate salt and a carboxylic acid.

Examples 4.4 and 4.5 illustrate the increase in activity and/or selectivity when palladium carboxylate catalysts containing non-cyclopalladatable carboxylate anions derived from carboxylic acids that are triply substituted at the alpha-carbon atom relative to the carboxylate group, with the carboxylic acids also containing at least one beta-carbon atom, are used instead of palladium carboxylate catalysts containing non-cyclopalladatable carboxylate anions derived from carboxylic acids devoid of such triply substituted carboxylate groups, as in examples 4.1-4.3.

Examples 4.2, 4.3, 4.5, and 4.6 illustrate the increase in activity and sometimes also selectivity when palladium carboxylate catalysts containing at least one non-cyclopalladatable carboxylate anion derived from a strongly acidic carboxylic acid, i.e. with an acidity constant that is equal or less than the acidity constant average of acetic acid and 2,2,2-trifluoroacetic acid, with aforementioned acidity constant average being quantified as $(pK_a^{acetic\ acid} + pK_a^{trifluoroacetic\ acid})/2$ are used instead of palladium carboxylate catalysts containing non-cyclopalladatable carboxylate anions derived from carboxylic acids with an acidity constant that is greater than this acidity constant average, as in examples 4.1 and 4.4. Comparison of example 4.7 with example 3.15 illustrates that palladium dicarboxylate catalysts derived from a carboxylic acid such as trifluoroacetic acid, which has an acidity constant that is less than an acidity constant in the range between that of acetic acid and 2,2,2-trifluoroacetic acid, perform well under relatively high (partial) pressures of oxygen (2-20 bar; example 4.7), but do not perform well under conditions of relatively low (partial) pressures of oxygen (0.2-2 bar; 3.15).

The data in Table 4 also illustrate the control of activity and selectivity by the substituent pattern of a ligand (cf. example 4.3 with 4.7; example 4.8 with 4.9).

Furthermore, the data in Table 4 illustrate that activity and selectivity (cf. example 1 with 2; example 1 with 3; example 2 with 3; example 1 with 5; example 1 with 6) may benefit from the addition of a strong acid to a palladium carboxylate catalyst.

TABLE 4

| Example: | 1 | 2 | 3 |
|---|---|---|---|
| Pd salt (mol %): | $Pd[MeCO_2]_2$ (0.5) | $Pd[MeCO_2]_2$ (0.5) | $Pd[MeCO_2]_2$ (0.5) |
| Additive (mol %): | — | $CF_3CO_2H$ (0.5) | $CF_3CO_2H$ (1.0) |
| Ligand: | pyridine | pyridine | pyridine |
| Yield (%) 2334 + 3344: | 0.92 | 3.56 | 9.62 |
| Yield Bald (%): | 0.35 | 0.99 | 0.45 |
| Regioselectivity (%): | 88 | 88 | 85 |
| Chemoselectivity (%): | 73 | 78 | 96 |

| Example: | 4 | 5 | 6 |
|---|---|---|---|
| Pd salt (mol %): | $Pd[tBuCO_2]_2$ (0.5) | $Pd[MeCO_2]_2$ (0.5) | $Pd[MeCO_2]_2$ (0.5) |
| Additive (mol %): | — | $PhCF_2CO_2H$ (1.0) | $C_6F_5CO_2H$ (1.0) |
| Ligand: | pyridine | pyridine | pyridine |
| Yield (%) 2334 + 3344: | 1.20 | 8.07 | 3.53 |
| Yield Bald (%): | 0.33 | 0.89 | 0.47 |
| Regioselectivity (%): | 95 | 89 | 88 |
| Chemoselectivity (%): | 78 | 90 | 88 |

| Example: | 7 | 8 | 9 |
|---|---|---|---|
| Pd salt (mol %): | $Pd[MeCO_2]_2$ (0.5) | $Pd[tBuCO_2]_2$ (0.5) | $Pd[tBuCO_2]_2$ (0.5) |
| Additive (mol %): | $CF_3CO_2H$ (1.0) | — | — |
| Ligand: | 4-CF$_3$-pyridine | 4-CF$_3$-pyridine | 3,5-bis(CF$_3$)-pyridine |

TABLE 4-continued

| Yield (%) 2334 + 3344: | 8.01 | 1.00 | 1.70 |
|---|---|---|---|
| Yield Bald (%): | 1.02 | 0.33 | 0.55 |
| Regioselectivity (%): | 85 | 96 | 93 |
| Chemoselectivity (%): | 89 | 75 | 76 |

Comparative Experiments B.1-B.4

CDC without solvent using various carboxylate anions at low pressure, no ligand or ligand with N/Pd molar ratio is 2/1.

A mixture of ortho-xylene (2.0 mL) without or with 4-(trifluoromethyl)pyridine as ligand (1.0 mol % of N-donor atoms), and palladium carboxylate (0.5 mol % of Pd) was stirred for 3 hrs at 85° C. (external temperature) in a reaction tube under 1 bar $O_2$. The reaction mixture was diluted and a sample was subsequently analyzed by GC, using hexadecane as internal standard. The results are shown in Table 5.

TABLE 5

| | Comparative Experiment: | | | |
|---|---|---|---|---|
| | B.1 | B.2 | B.3 | B.4 |
| Palladium carboxylate catalyst: | Pd[tBuCO$_2$]$_2$ | Pd[tBuCO$_2$]$_2$ | Pd[3,5-(CF$_3$)$_2$C$_6$H$_3$CO$_2$]$_2$ | Pd[3,5-(CF$_3$)$_2$C$_6$H$_3$CO$_2$]$_2$ |
| 4-(Trifluoromethyl)pyridine: | — | 2 eq/Pd | — | 2 eq/Pd |
| Yield (%) 2334 + 3344: | 0.00 | 0.13 | 0.22 | 0.00 |
| Yield (%) Bald: | 0.42 | 0.03 | 0.00 | 0.00 |
| Regioselectivity (%): | — | 92 | 55 | — |
| Chemoselectivity (%): | 0 | 81 | 100 | — |

Comparison of examples 3.1 and 3.6 with comparative experiments B.1 and B.3, respectively, illustrates that activities increase strongly on increasing the N/Pd ratio from 0 to 1, with good or excellent selectivities being obtained. Comparison of examples 3.1 and 3.6 with comparative experiments B.2 and B.4, respectively, illustrates that activities increase strongly on decreasing the N/Pd ratio from 2 to 1, with good or excellent selectivities being obtained.

Comparative Experiments C.1-C.4

CDC without solvent using various carboxylate anions at high pressure, no ligand or ligand with N/Pd molar ratio is 2/1.

A mixture of ortho-xylene (1.0 mL) without or with pyridine as ligand (1.0 mol % of N-donor atoms), palladium carboxylate (0.5 mol % of Pd), and optionally a carboxylic acid additive (amount indicated below), was stirred for ~2.5 hrs at 85° C. (external temperature) in an autoclave under 11 bar $O_2$. The reaction mixture was diluted and a sample was subsequently analyzed by GC, using hexadecane as internal standard. The results are shown in Table 6.

TABLE 6

| | Example: | | | |
|---|---|---|---|---|
| | C.1 | C.2 | C.3 | C.4 |
| Palladium carboxylate catalyst: | Pd[MeCO$_2$]$_2$ | Pd[MeCO$_2$]$_2$ | Pd[tBuCO$_2$]$_2$ | Pd[MeCO$_2$]$_2$ (0.5) |
| Additive (mol %): | — | CF$_3$CO$_2$H (1.0) | — | PhCF$_2$CO$_2$H (1.0) |
| Pyridine: | — | — | — | — |
| Yield (%) 2334 + 3344: | 0.21 | 3.17 | 0.00 | 1.33 |
| Yield (%) Bald: | 0.63 | 0.06 | 0.59 | 0.03 |
| Regioselectivity (%): | 74 | 60 | — | 71 |
| Chemoselectivity (%): | 25 | 98 | 0 | 98 |

| | Example: | | | |
|---|---|---|---|---|
| | C.5 | C.6 | C.7 | C.8 |
| Palladium carboxylate catalyst: | Pd[MeCO$_2$]$_2$ | Pd[MeCO$_2$]$_2$ | Pd[tBuCO$_2$]$_2$ | Pd[MeCO$_2$]$_2$ (0.5) |
| Additive (mol %): | — | CF$_3$CO$_2$H (1.0) | — | PhCF$_2$CO$_2$H (1.0) |
| Pyridine: | 2 eq/Pd | 2 eq/Pd | 2 eq/Pd | 2 eq/Pd |
| Yield (%) 2334 + 3344: | 0.26 | 1.81 | 0.09 | 2.27 |
| Yield (%) Bald: | 0.24 | 0.76 | 0.10 | 0.63 |
| Regioselectivity (%): | 86 | 89 | 88 | 89 |
| Chemoselectivity (%): | 52 | 70 | 46 | 78 |

Comparison of examples 4.1, 4.3, 4.4, and 4.5 with comparative experiments C.1, C.2, C.3, and C.4, respectively, illustrates that activities increase strongly on increasing the N/Pd ratio from 0 to 1, with good or excellent selectivities being obtained. Comparison of examples 4.1, 4.3, 4.4, and 4.5 with comparative experiments C.5, C.6, C.7, and C.8, respectively, illustrates that activities increase strongly on decreasing the N/Pd ratio from 2 to 1, with good or excellent selectivities being obtained.

Comparative Experiment D

CDC using a beta-eliminatable ligand, N/Pd molar ratio is 1/1.

A mixture of ortho-xylene (1.0 mL), dry propylene carbonate (1.0 mL), Pd[MeCO$_2$]$_2$ (1.0 mol %), CF$_3$CO$_2$H (0.8 mol %), and tripropylamine (1.0 mol % of N-donor atoms) was stirred for 16 hrs at 85° C. (external temperature) in a reaction tube under 1 bar O$_2$. The reaction mixture was diluted and a sample was subsequently analyzed by GC, using hexadecane as internal standard. A slight deficiency of CF$_3$CO$_2$H relative to the amount required to fully convert Pd[MeCO$_2$]$_2$ into Pd[MeCO$_2$][CF$_3$CO$_2$] was used in order to allow accurate comparison of the results with those shown in Table 1. No activity was obtained. Beta-hydride elimination of a trialkylamine as nitrogen donor ligand has been described in *Chemistry* 2011, 17, 3091. Comparison of example 1.10 based on quinuclidine as an example of a non-beta-eliminatable trialkylamine ligand with comparative experiment D illustrates that activities increase strongly on using a non-beta-eliminatable ligand instead of a beta-eliminatable ligand, with good selectivities being obtained.

Comparative Experiment E

CDC using a cyclopalladatable ligand, N/Pd molar ratio is 1/1.

A mixture of ortho-xylene (1.0 mL), dry propylene carbonate (1.0 mL), Pd[MeCO$_2$]$_2$ (1.0 mol %), CF$_3$CO$_2$H (0.8 mol %), and 2-(tert-butyl)pyridine (1.0 mol % of N-donor atoms) was stirred for 16 hrs at 85° C. (external temperature) in a reaction tube under 1 bar O$_2$. The reaction mixture was diluted and a sample was subsequently analyzed by GC, using hexadecane as internal standard. A slight deficiency of CF$_3$CO$_2$H relative to the amount required to fully convert Pd[MeCO$_2$]$_2$ into Pd[MeCO$_2$][CF$_3$CO$_2$] was used in order to allow accurate comparison of the results with those shown in Table 1. No activity was obtained. Cyclopalladation of 2-(tert-butyl)pyridine as nitrogen donor ligand has been described in *Angew. Chem. Int. Ed.* 2012, 51, 2225. Comparison of examples 1.1-1.9 based on non-cyclopalladatable pyridines as ligand with comparative experiment E illustrates that activities increase strongly on using a non-cyclopalladatable ligand instead of a cyclopalladatable ligand, with good or excellent selectivities being obtained.

Comparative Experiment F

CDC using a cyclopalladatable carboxylate anion, N/Pd molar ratio is 1/1.

A mixture of ortho-xylene (2.0 mL), Pd[MeCO$_2$]$_2$ (0.5 mol %), 4-(trifluoromethyl)benzoic acid (1.0 mol %), and 4-(trifluoromethyl)pyridine (0.5 mol % of N-donor atoms) was stirred for 3 hrs at 85° C. (external temperature) in a reaction tube under 1 bar O$_2$. The reaction mixture was diluted and a sample was subsequently analyzed by GC, using hexadecane as internal standard. The combined 2334+ 3344 yield was 0.19%. Cyclopalladation of benzoate anions has been described in *J. Am. Chem. Soc.* 2008, 130, 14082. Direct evidence for cyclopalladation of 4-(trifluoromethyl) benzoic acid was obtained by heating Pd[MeCO$_2$]$_2$ (0.037 mmol), 4-(trifluoromethyl)benzoic acid (0.075 mmol), and 4-(trifluoromethyl)pyridine (0.038 mmol) in 0.8 mL toluene-d$_8$ for 15 hrs at 85° C. (external temperature) in a reaction tube, followed by removal of traces of metallic palladium by filtration and $^1$H-NMR analysis of the filtrate. The complex NMR spectrum showed clear conversion of the benzoate unit. After evaporation of toluene-d$_8$ and redissolution of the yellow-white powder in pyridine-d$_5$, a much simpler NMR spectrum was obtained with a characteristic high field singlet at 6.57 ppm, corresponding to the proton positioned ortho with respect to CF$_3$-bearing and palladated carbon atoms in a cyclopalladated 4-(trifluoromethyl)benzoate complex with pyridine ligands, having a pyridine positioned cis with respect to the palladated carbon atom and perpendicular with respect to the square plane around Pd. Comparison of example 3.11 based on non-cyclopalladatable 3-(trifluoromethyl)benzoate as carboxylate anion with comparative experiment F illustrates that activities increase strongly on using a non-cyclopalladatable carboxylate anion instead of a cyclopalladatable carboxylate anion, with good or excellent selectivities being obtained. The much higher yield obtained with 3-(trifluoromethyl)benzoate instead of 4-(trifluoromethyl)benzoate illustrates that the susceptibility of a carboxylate anion towards cyclopalladation can be suppressed by introducing electron-withdrawing substituents provided these are suitably positioned relative to the carbon atom undergoing cyclopalladation.

The invention claimed is:

1. Process for producing biaryl compounds by aerobic cross dehydrogenative coupling (CDC) of two arene groups comprising at least one aryl carbon-hydrogen bond, in the presence of a catalyst system comprising a palladium salt comprising at least one non-cyclopalladatable carboxylate anion and one or more non-beta-eliminatable, non-cyclopalladatable ligands comprising at least one N-donor atom, the one or more ligands having a 0.5/1-1.5/1 molar ratio of N-donor atoms relative to the Pd atoms.

2. Process according to claim 1, wherein the molar ratio of N-donor atoms relative to the Pd atoms is between 0.7/1 and 1.3/1.

3. Process according to claim 1, wherein the molar ratio of N-donor atoms relative to the Pd atoms is between 0.8/1 and 1.2/1.

4. Process according to claim 1, wherein aliphatic cyclic or non-cyclic primary, secondary or tertiary amines, aromatic N-heterocycles and/or benzofused derivatives thereof are used as the one or more ligands.

5. Process according to claim 4, wherein pyridines, pyridazines, pyrimidines, pyrazines, triazines, imidazoles, triazoles, oxazoles, 4,5-dihydrooxazoles, isoxazoles, 4,5-dihydroisoxazoles, and 5,6-dihydro-4H-1,3-oxazines or quinolines, isoquinolines, cinnolines, phthalazines, quinazoline, quinoxalines, 1H-benzo[d]imidazoles, 1H-benzo[d][1,2,3]triazoles, benzo[d]oxazoles, benzo[d]isoxazoles and 4H-benzo[e][1,3]oxazines and/or benzofused derivatives thereof are used as the one or more ligands.

6. Process according to claim 4, wherein pyridines, pyridazines, pyrimidines, pyrazines, triazines, quinolines, isoquinolines, cinnolines, phthalazine, quinazoline, and quinoxalines and/or benzofused derivatives thereof are used as the one or more ligands.

7. Process according to claim 1, wherein the process is carried out under a (partial) pressure of oxygen of 0.2-2 bar, and wherein a catalyst system is used comprising a palladium salt comprising at least one non-cyclopalladatable carboxylate anion derived from a carboxylic acid that is triply substituted at the alpha-carbon atom relative to the carboxylate group, with the carboxylic acid also containing at least one beta-carbon atom.

8. Process according to claim 7, wherein the carboxylate anion is derived from a 2,2-dialkylalkanoic acid, 2-fluoro-2-alkylalkanoic acid, 2,2-difluoroalkanoic acid, 2,2-difluoro-2-arylacetic acid, with the alkanoic acid containing at least one beta-carbon atom.

9. Process according to claim 7, wherein the carboxylate anion is derived from pivalic acid, 3,3,3-trifluoro-2-methyl-2-(trifluoromethyl)propanoic acid, 3,3,3-trifluoro-2,2-bis(trifluoromethyl)propanoic acid, and 2,2-difluoro-2-phenylacetic acid.

10. Process according to claim 1, wherein the process is carried out under a (partial) pressure of oxygen of 0.2-2 bar, and wherein a catalyst system is used comprising a palladium salt comprising at least one non-cyclopalladatable carboxylate anion derived from a carboxylic acid with an acidity constant in between that of acetic acid and 2,2,2-trifluoroacetic acid, with aforementioned acidity constant meaning the acidity constant average $(pK_a^{acid\ 1}+pK_a^{acid\ 2})/2$ in case of two different carboxylate anions.

11. Process according to claim 10, wherein the carboxylate anion is derived from 2,2-difluoroacetic acid, 2,2-difluoropropionic acid, 3,3,3-trifluoro-2-methyl-2-(trifluoromethyl)propanoic acid, 3,3,3-trifluoro-2,2-bis(trifluoromethyl)propanoic acid, 2,3,4,5,6-pentafluorobenzoic acid, 2,2-difluoro-2-phenylacetic acid, 2-(2,3,4,5,6-pentafluorophenyl)acetic acid 2,4-dinitrobenzoic acid, 2,5-dinitrobenzoic acid, and 3,4-dinitrobenzoic acid.

12. Process according to claim 1, wherein the process is carried out under a (partial) pressure of oxygen of 2-20 bar, and wherein a catalyst system is used comprising a palladium salt comprising at least one non-cyclopalladatable carboxylate anion derived from a strongly acidic carboxylic acid, i.e. with an acidity constant that is equal or less than the acidity constant average of acetic acid and 2,2,2-trifluoroacetic acid, with aforementioned acidity constant average being quantified as $(pK_a^{acetic\ acid}+pK_a^{trifluoroacetic\ acid})/2$.

13. Process according to claim 12, wherein the carboxylate anion is derived from trifluoroacetic acid, 3,3,3-trifluoro-2,2-bis(trifluoromethyl)propanoic acid, 3,3,3-trifluoro-2-(trifluoromethyl)propanoic acid, and 2,2-difluoro-2-phenylacetic acid.

14. Process according to claim 1, wherein at most 50 wt % of solvent is used, based on the total reaction mass.

15. Process according to claim 1, wherein at most 10 wt % of solvent is used, based on the total reaction mass.

\* \* \* \* \*